US 6,202,469 B1

(12) United States Patent
Nakamura et al.

(10) Patent No.: US 6,202,469 B1
(45) Date of Patent: *Mar. 20, 2001

(54) GAS CONCENTRATION DETECTING DEVICE

(75) Inventors: Satoshi Nakamura; Masanori Yamada; Michihiro Wakimoto; Daisuke Makino, all of Nishio; Hideomi Kawachi, Nagoya; Toshihiro Sakawa, Toyohashi, all of (JP)

(73) Assignee: Denso Corporation, Kariya (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/953,480

(22) Filed: Oct. 17, 1997

(30) Foreign Application Priority Data

Oct. 17, 1996 (JP) .................................................. 8-297586

(51) Int. Cl.$^7$ .................................................. G01N 27/12
(52) U.S. Cl. .......................................... 73/23.31; 73/118.1
(58) Field of Search ............................... 73/23.31, 23.32, 73/118.1; 60/276

(56) References Cited

U.S. PATENT DOCUMENTS

| 2,935,866 | * | 5/1960 | Schmidt et al. ...................... 73/23.31 |
| 3,522,010 | * | 7/1970 | Archer .................................. 73/23.31 |
| 3,768,259 | * | 10/1973 | Carnahan et al. ....................... 60/276 |
| 4,184,934 | * | 1/1980 | Bode et al. .......................... 73/23.31 |
| 4,199,424 | * | 4/1980 | Teitelbaum .......................... 73/23.31 |
| 4,225,842 | * | 9/1980 | Schlesselman et al. ............. 73/23.31 |
| 4,303,613 | * | 12/1981 | Yasuda et al. ....................... 73/23.32 |
| 4,308,518 | * | 12/1981 | Hattori et al. ........................ 73/23.31 |
| 4,532,492 | * | 7/1985 | Esper et al. .......................... 73/23.31 |
| 5,031,445 | * | 7/1991 | Kato et al. ............................ 73/23.31 |
| 5,073,247 | | 12/1991 | Weyl . |

FOREIGN PATENT DOCUMENTS

| 90 14 826 | 2/1992 | (DE) . |
| 53-103784 | 8/1978 | (JP) . |
| 55-39099 | 3/1980 | (JP) . |
| 55-39100 | 3/1980 | (JP) . |
| 55-17164 | 4/1980 | (JP) . |
| 59-194061 | 12/1984 | (JP) . |
| 9-5270 | 1/1997 | (JP) . |
| 9-5277 | 1/1997 | (JP) . |
| 9-5278 | 1/1997 | (JP) . |

OTHER PUBLICATIONS

Patent Abstracts of Japan, vol. 14, No. 189 (P–1037), Apr. 17, 1990, & JP 02 035349.
Patent Abstracts of Japan, vol. 10, No. 160 (P–465), & JP 61 013147 Jan. 1986.
Patent Abstracts of German Appln., DE9014826.

\* cited by examiner

*Primary Examiner*—Eric S. McCall
(74) *Attorney, Agent, or Firm*—Pillsbury Winthrop LLP

(57) ABSTRACT

A gas concentration detecting device for detecting the concentration of a component, such as an oxygen in an exhaust gas of an internal combustion engine. The device has a concentration detecting body 2 for detecting the oxygen and a cover 3 of a double wall structure which is for encircling the portion of the detecting body opened to the flow of the exhaust gas to be detected. The cover 3 has, at its axial tip end wall, a plurality of holes 33 and 34 arranged in such a manner that one of the holes functions as a gas inlet hole and the other hole functions as a gas outlet hole in order to cause the gas to be smoothly ventilated. The cover has, at its side, a wall of a closed structure with no hole for the passage of the gas, which is effective for preventing the cover 3 and the detecting body 2 from being cooled by the exhaust gas, thereby enhancing a heat retaining capacity, thereby preventing particulates from being deposited.

12 Claims, 10 Drawing Sheets

GAS CONCENTRATION DETECTING DEVICE

BACKGROUND OF THE INVENTION

1. Field of the Invention

The present invention relates to a gas concentration detecting device for detecting the concentration of a particular gas component in a gas to be detected. In particular, the present invention relates to a gas concentration detecting device suitable for detecting the concentration of a gas such as oxygen in an exhaust gas of an internal combustion engine.

2. Description of Related Art

A known gas concentration detecting device is shown in FIG. 1. The device shown in FIG. 1 is mounted to a wall of an exhaust pipe of an internal combustion engine and used for detecting the concentration of oxygen in an exhaust gas in an exhaust gas recirculating (EGR) system for an internal combustion engine to allow a feedback control of a recirculated exhaust gas (EGR gas) in accordance with the detected concentration of the gas. The gas concentration detecting device includes a housing 92 having a flange 91 which is connected to a wall of an exhaust gas of an internal combustion engine. Inside the housing 92, a gas concentration detecting body 93 of a tubular shape is stored, so that a lower half part of the body 93 is projected downwardly from the housing 92 toward the space inside the exhaust pipe P, while being encircled by a cover unit 94. The gas concentration detecting body 93 is formed as a tubular member made of a solid electrolyte such as a zirconia having an inner and outer surfaces on which electrodes made from a material such as a platinum are formed. Furthermore, a heater 95 is arranged in the gas concentration detecting body 93 for heating the latter so that the precision of detection is increased.

The cover unit 94, which is to allow the gas concentration detecting body 93 to be thermally insulated and prevents the body 93 from being subjected to a mechanical impact force, is formed as a double tube structure including an inner tube 94a and an outer tube 94b. These tubes 94a and 94b are, at their cylindrical walls, formed with gas vent holes 941 and 942 in an alternating manner, so that the speed of the inflow of the exhaust gas is reduced, thereby preventing the electrodes from being degraded. As is well known, in a diesel engine, a temperature of the exhaust gas is reduced and an amount of the exhaust gas is increased in comparison with the gasoline internal combustion engine. As a result, in the diesel engine, the gas concentration detecting body may be quickly cooled if contact between the exhaust gas and the gas concentration detecting body 93 occurs at the outer surface of the body. The cover 94 is designated to prevent such a cooling of the body 93 as much as possible.

Namely, the arrangement of the cover 94 is such that it encircles the end of the gas concentration detecting body 93, which is in the flow of exhaust gas, thereby maintaining the temperature of the body 93.

However, in the structure of the gas concentration detecting device in the prior art, as shown in FIG. 1, the gas vent holes 941 and 942 in the peripheral wall of the cover 94 are opened in the direction of the flow of the exhaust gas. As a result, the flow of the exhaust gas is able to pass through the cover without being subjected to a substantial speed reduction. As a result, in a diesel engine where the gas concentration detecting device having the above mentioned cover unit 94 is employed, it its likely that a heat retaining capacity of the gas concentration detecting body 93 due to the cover unit 94 is not sufficiently high so that the temperature of the surface of the gas concentration detecting body 83, as well as the temperature of the cover unit 94 itself, are low which may cause particulates in the exhaust gas in the diesel engine to be attached or deposited on the surface of the cover. These particulates includes components such as soot and soluble organic fraction (SOF). The SOF has an increased value of a viscosity, which may cause the soot to be attached to the surface of the cover unit 94 via the SOF, when the temperature of the surface is low, due to the fact that the lower temperature causes the SOF to be less volatile. Such attached and deposited particulates are partly subjected to combustion by contacting high temperature exhaust gas during a high load operation of the engine, which causes the composition of the exhaust gas, i.e., an oxygen concentration to be varied in the atmosphere around the gas concentration detecting body 93, which results in an error in the oxygen concentration measurement. Furthermore, the gas vent holes 941 and 942 are likely to be clogged by particulates, which causes the speed of the passage of the gas to be reduced, thereby reducing measuring response speed and generating a measuring error. In order to obviate these problems, a solution for increasing the heat generated by the heater can be employed. However, this solution necessitate an increased load in the heater and an increased electric power consumption by the heater.

Japanese Utility Model Publication No. 53-103784 proposes a oxygen concentration sensor, wherein a cover has a closed end of an increased heat mass, which can increase a heat retaining property with respect to a change in the temperature of the exhaust gas. However, in this construction the cover unit has, at its side wall, gas vent holes which cause the above problems to still be generated.

In view of the above problems, the inventors conceived a solution in that the cover unit is, at its side wall, free from any gas passage hole, while gas passage holes are formed at tip end of the cover unit, so that the amount of the exhaust gas in contact with the gas concentration detecting body is reduced, thereby preventing an occurrence of a flow of the exhaust gas transverse the cover, thereby preventing the cover unit from being overly cooled. U.S. Pat. No. 5,073,247 discloses such a construction of a cover unit having a gas vent hole only at end wall of the cover, i.e., no provision of vent hole at side wall of the cover, although the subject of this prior art is not at all related to a cooling of the gas concentration detecting body and the cover. However, in this patent, only one gas passage hole is provided at the tip end of the cover, so that an inflow of the gas to the space inside the cover and an outflow of the gas from the space are occurred simultaneously via the single hole, which causes a gas ventilation to be not smooth between the inflow and outflow of the gas, thereby reducing the response speed in a measurement.

SUMMARY OF THE INVENTION

An object of the present invention is to provide a gas concentration detecting device capable of overcoming the above mentioned difficulties in the prior art.

Another object of the present invention is to provide a gas concentration detecting device capable of increasing a heat retaining capacity, thereby preventing particulates from being attached and deposited and preventing the measuring precision from being reduced, while keeping a desired speed of the response in a measurement.

According to the first invention, a device is provided for detecting a concentration of a component in a gas to be detected, comprising:

a gas concentration detecting body which is adapted to be contacted with the gas for generating an electric signal indicative of the concentration of the component, and a cover for covering the portion of the detecting body for preventing the detecting body from being directly subjected to the exhaust gas to be detected;

said cover having, at its axial end, holes functioning as inlet and outlet openings for the gas to be detected while said cover forms, at locations other than said axial end, a closed wall not having any opening for a passage of the gas to be detected.

In the above structure, the openings are formed only at the axial tip end of the cover, which is effective for suppressing a cooling of the cover and the gas concentration detecting body by means of the inflow or outflow of the exhaust gas over the prior art construction having gas ventilation openings formed also at a side wall of the cover. Thus, the present invention makes it possible to reduce a load of the heater for heating the detecting body, while increasing a heat retaining capacity, thereby preventing a deposition of particulates, which would otherwise cause a measuring error to occur. Furthermore, due to the provision of the inlet and outlet openings only at the axial end of the cover, the flow of the exhaust gas is prevented from being directly introduced into the openings, which makes it less likely that the openings are clogged by the particulates. Furthermore, due to the provision of a plurality of openings, one of the openings can function as in inlet for the gas to be detected, while the other opening function as an outlet. Thus, a smooth ventilation of the gas is obtained, thereby increasing a detecting response, in comparison with the structure where only one opening is provided.

According to the second invention, the cover may have, at its axial end, single hole having a throttle portion which divides the hole into parts functioning as inlet and outlet openings for the gas to be detected, while said cover forms, at locations other than said end portion, a closed wall not having any opening for a passage of the gas to be detected.

In the structure, substantially the same advantageous effect as that in the first invention is obtained. Furthermore, by the provision of the throttle portion, the single hole is divided into openings, one of which functions as an inlet opening while the other opening functions as an outlet opening. As a result, a smooth ventilation of the gas is obtained, resulting in an increased response speed in measurement.

Preferably, said cover is formed as a double wall structure having an inner and outer tube of different diameter while arranged concentrically with each other. Due to the double tube structure of the cover around the detecting body, a further enhanced heat insulating effect is obtained. Furthermore, said cover may be formed as a multiple wall structure having an inner and outer tubes of different diameters and at least one intermediate tube arranged between the inner and the outer tubes, these inner and outer and intermediate tubes being arranged concentrically.

Preferably, in the case of a multiple tube structure of the cover, only the axial end of the inner tube forms an end wall, where said inlet and outlet openings are formed, and any tube located outwardly from the inner tube are fully opened at the axial end. Due to the fully opened structure of the outer tube, it is possible to prevent the heat at the opening as the inlet or outlet of the gas to be detected from being discharged to the outer tube and from being emitted to the side wall of the outer tube. Thus, a high temperature is maintained at the location adjacent the openings, thereby increasing a heat retaining capacity.

In the case of a multiple tube structure, it is possible to arrange such that the inner tube is, at its axial end, under a non-contacted condition with the axial end of an outer tube. By this structure, an escape of heat from the tip end of the inner tube to the tip end of the outer tube is prevented, thereby maintaining a high temperature at the location adjacent to the openings, thereby maintaining an increased heat retaining capacity.

Preferably, said inner tube is tapered toward said axial end. As result of this, a reduction of the inner volume is obtained, resulting in a very smooth ventilation of the gas inside the inner tube, which assists in increasing a response speed.

BRIEF EXPLANATION OF ATTACHED DRAWINGS

DETAILED EXPLANATION OF EMBODIMENTS

Now, embodiments of the present invention directed to a solution of the problem will be explained.

Figure 1:
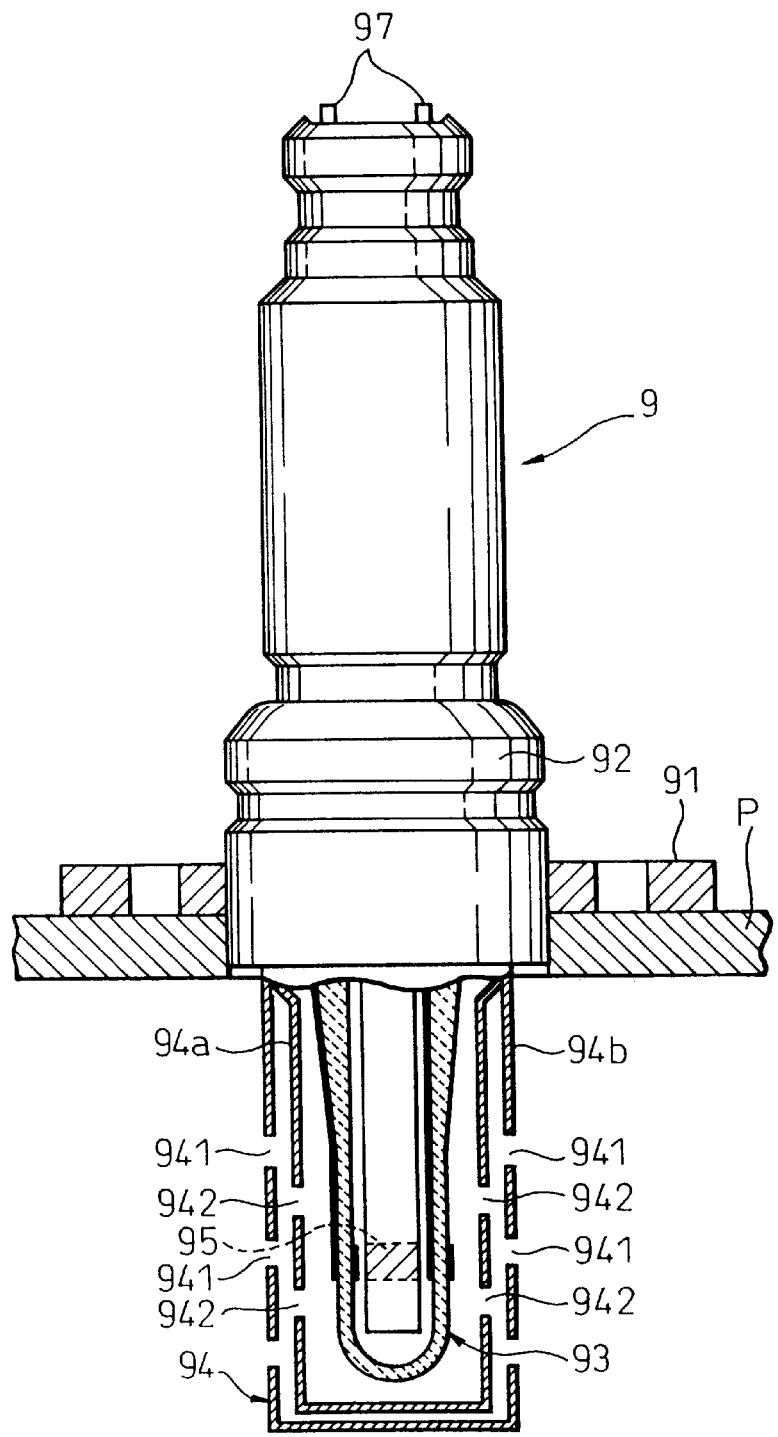
FIG. 1 is a schematic cross sectional view of an oxygen concentration detecting device in a prior art.
Figure 2:
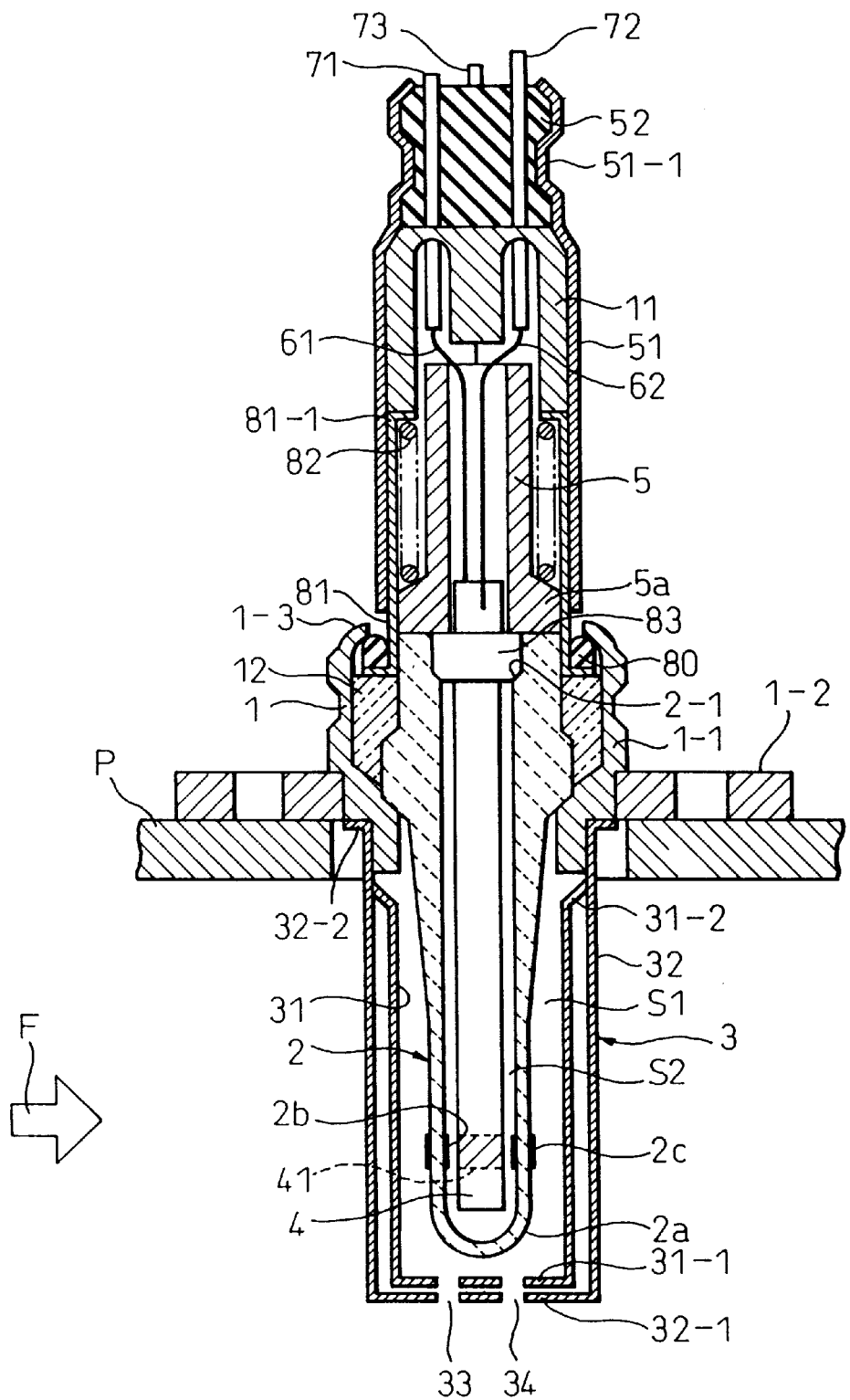
FIG. 2 is a schematic cross sectional view of an oxygen concentration detecting device in a first embodiment of the present invention.

FIG. 2 shows a first embodiment of oxygen sensor according to present invention adapted to be mounted to an exhaust pipe of a diesel engine. The oxygen sensor includes a tubular housing 1 which is fixed to a wall P of an exhaust pipe of the engine. Namely, the housing 1 is formed with a flange portion 1-1, which is axially engaged with and fixed to a flange plate 1-2, which is connected to the wall P of the exhaust pipe by any suitable means. Inside the housing 1, a gas concentration detecting body 2 of a tubular shape is arranged. The detecting body 2 has an upper half part fixed to the housing 1 and a lower half part extended into a space inside the exhaust pipe P in such a manner that contact occurs between the flow of the exhaust gas and the body 2. A cover unit or assembly 3 is provided for storing therein the lower half of the detecting body 2. The detecting body 2 is formed with an axially elongated inner space with a closed bottom, in which a heater 4 of a rod shape is extended. A tubular cap 5 made of a ceramic material is arranged at the top of the detecting body 2, which is housed in a sheath member 51 made of a metal material. An electric insulating member 52 is fitted to a top end of the sheath member 51.

The gas concentration detecting body 2 is formed with an oxygen ion conductive solid electrolyte body 2a, such as a zirconia body, of a tubular shape and electrodes 2b and 2c formed at faced positions on an inner and outer surfaces of the body 2 at positions. In a well known manner, a diffusion resistance layer (not shown) made of a material such as porous alumina is formed on the outer surface of the solid electrolyte body 2a in such a manner that the exhaust gas is contacted with the outer electrode 2c after passed through the diffusion resistance layer. The electrodes 2b and 2c are connected, via conductive layers on the surface 2a of the detecting body 2, to lead wires 61 and 62, respectively, which are connected to terminals 71 and 72, respectively held by the electric insulating member 52.

A metallic tube 81 is arranged between the tubular cap 5 and the cover 51. The tube 81 has a top end which is in end to end contact with a sleeve 11 made of a ceramic material and a bottom end which is inserted to the housing 1 via a seal ring 80, while an insulating material 12 fills a space between the members 1, 2 and 81. As shown in FIG. 2, the tube 81 has, at its bottom end portion, a C-cross sectional shaped portion, to which the seal ring 80 is arranged. Furthermore, the housing 1 has a top edge portion 1-3, which is radially inwardly crimped, so that the tube 81 together with the ring 80 is fixedly connected to the housing 1.

A coil spring 82 is arranged between an upper flange portion 81-1 of the tube 81 and a lower flange portion 5a of the cap 5, so that a spring force is created, which causes the upper cap 11 to be in end-to-end contact with the detecting body 2. Furthermore, a crimping is done at a portion 51-1 of the upper end of the cover 51, so that the cover 51 and the electric insulating member 52 are fixedly connected with each other. The axial position of the insulating member 52 is such that the coil spring 82 is subjected to compression, so as to generate a spring force, which causes the cap 5 to be pressed to the detecting body 2. A guide ring 83, which is under an axial end-to-end contact with the cap 5, is fixed to an upper end of the heater rod 4. As a result, the spring force by the coil spring 82 also causes the guide ring 83 to be moved downwardly. In other words, the guide ring 83 is urged downwardly to made a contact with a shoulder portion 2-1, thereby obtaining axially fixed location of the heater rod 4 with respect to the detecting body 2.

A small gap exists between the lower end of the cover 51 and the tube 81 so that leakage of atmospheric air occurs, via the gap between the tubular body 11 and upper end of the tube 81, through a space inside the tubular member 11, a space inside the cap 5 and a fitting gap between the guide ring 83 of the heater 4 and the detecting body 2, into the space inside the detecting body 2.

The heater 4 arranged in the hollow space inside the solid electrolyte member 2a is for heating the detecting body 2, so as to increase the precision of measurement. The heater 4 is for heating the detecting body 2 for increasing its sensitivity and is formed as a rod made of a material such as an alumina on which a heating element constructed, for example, of a nichrome wire is arranged at a location on the rod opposite the electrodes 2b and 2c as shown in FIG. 2. The heater 4 is in electrical connection with a terminal 73 which is held by the insulating member 52.

Figure 3:
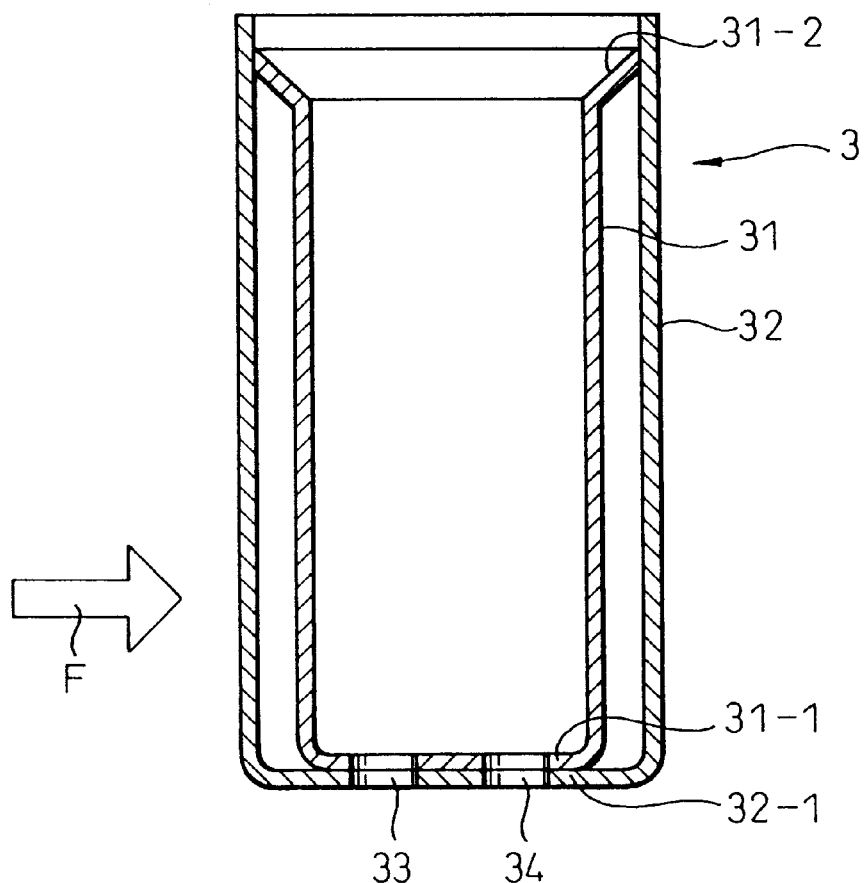
FIG. 3 is a cross sectional view of a cover assembly in the device in FIG. 2.

The cover unit 3 is constructed as a double tube structure including an inner tube 31 and an outer tube 32 of different diameters as shown in FIG. 3, which are concentrically arranged with each other. The inner and outer tubes 31 and 32 have flat or horizontally extending end parts 31-1 and 32-1, which are in a close face to face contact. The inner tube 31 has an upper bent portion 31-2, which is fixedly connected to an inner cylindrical surface of the outer tube 32. The outer tube 32 has an upper part which is inserted into the lower end of the housing 1 and which has a flange portion 32-2 which is fixedly connected to the housing 1.

Figure 4:
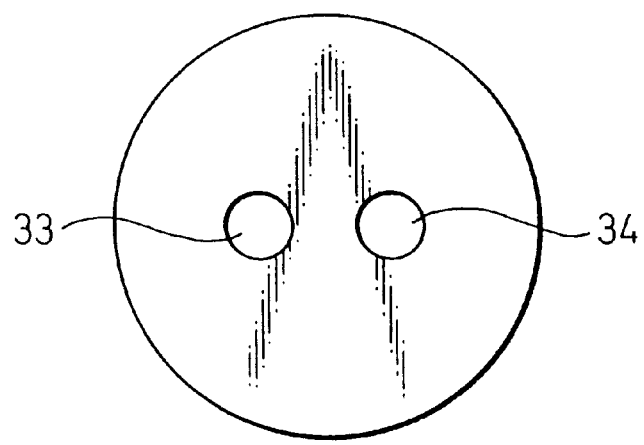
FIG. 4 is a bottom elevational view of the cover in FIG. 3.

As shown in FIGS. 3 and 4, the inner and outer tubes 31 and 32 have, at the bottom end portions 31-1 and 32-2, gas flow holes 33 and 34, which are spaced in a direction which is parallel to the direction of the flow of the exhaust gas in the exhaust pipe (P) of the internal combustion engine, while the openings 33 and 34 are opened to the space inside the cover unit 3 in a direction transverse to the direction of the flow of the exhaust gas as shown by an arrow F. The openings 33 and 34 are of the same shape (circular shape) and one of the openings functions as a gas inlet hole or passageway, while the other opening functions as a gas discharge hole or passageway. According to the present invention, the inner and the outer covers 31 and 32 are not, at the side or cylindrical wall thereof, equipped with any hole for a passage of the gas. In other words, an introduction of the exhaust gas from the internal combustion engine to the space inside the cover 3 occurs only through the gas communication holes 33 and 34 at the bottom walls 31-1 and 32-2.

Now, an operation of the gas concentration detecting device according to the first embodiment of the present invention is as follows. Under the condition of the detecting device as shown in FIG. 2, the exhaust gas from the internal combustion engine is introduced, via the gas communication hole 33 or 34, into the space S1 inside the cover unit 3 and is contacted with the surface of the detecting body 2. On the other hand, the atmospheric air is introduced into the space S2 inside the detecting body 2. The heater 4 heats the detecting body 2 to a predetermined temperature, while a predetermined voltage is applied across the electrodes 2b and 2c. As a result, the oxygen in the exhaust gas is passed through the diffusion resistance layer on the surface of the detecting body 2 and is first moved to the outer electrode 2c and is then moved, via the solid electrolyte body 2a, to the inner electrode 2b. Due to such a movement of the oxygen, an electric current, which is proportional to the concentration of the oxygen in the exhaust gas, is generated across the electrodes 2b and 2c. Thus, by detecting such an electric current, the oxygen density in the exhaust gas can be determined.

According to the present invention, the cover unit 3 is not, at the side wall thereof, formed with any gas vent hole, so that the detecting body 2 as well as the inner tube 31 are prevented from being directly subjected to the flow of the exhaust gas, thereby preventing a reduction of the surface temperature in the cover unit 3 and the detecting body 2, which otherwise occurs due to the inflow of the exhaust gas into the space inside the cover unit 3 or the outflow of the exhaust gas from the space. As a result, particulates are prevented from being attached or deposited on the cover unit 3 or detecting member 2, thereby preventing a measuring error from occurring.

Furthermore, according to present invention, the gas passage holes 33 and 34 are not directed to the direction of the flow of the exhaust gas, resulting in clogging of the holes 33 and 34 being less likely, which prevents a reduction in the flow of the exhaust gas. Furthermore, two gas passage holes 33 and 34 of the same shape are arranged in parallel to the direction F of the flow of the exhaust gas, which allows the functions of the holes 33 and 34 to be properly assigned such that one of the holes functions as a gas inlet hole, while the other one functions as a gas outlet hole. As a result, in comparison with the structure, where only one hole is provided, a smooth flow of the exhaust gas into or from the space inside the cover is obtained, which allows the speed of the ventilation of the gas in the cover to be promoted. Furthermore, due to the fact that inner and the outer tubes 31 and 32 of the cover unit 3 are under a contacted condition at the bottom ends of the tubes, it is possible to prevent the gas from remaining in the gap between the inner and the outer tubes 31 and 32, thereby increasing the response speed of detection.

The inventors have conducted a test of the improvement in a heat keeping performance of the oxygen detecting device according to present invention as explained above when the device is used in a diesel engine in such a manner that an exhaust gas contacts with the sensor under an idling condition of the diesel engine. In this test, as a cover unit 3, one having an axial length of 20 mm, an inner tube diameter of 7 mm and of an outer tube diameter of 9 mm was used. Furthermore, the diameter of the gas passage holes 33 and 34 was 2.5 mm. According to the result of the test, under the same electric current in the heater, the structure of the oxygen detecting device according to present invention can obtain a temperature increase of 75° C. at the surface of the detecting body and a temperature increase of 45° C. at the inner surface of the cover unit 3 were obtained in comparison with the structure of the oxygen concentration detecting device in prior art. In other words, according to present invention, an attachment as well as deposition of particulates can be highly reduced.

Furthermore, a 63% response speed was measured when the concentration of the oxygen in the exhaust gas is rapidly changed from 5% to 10%, which is expressed by the time which is necessary for obtaining a change in the concentration of 63% from the rapid temperature changing point in the oxygen density. According to the result of the test, an increase of the 63% response speed from 400 ms to 180 ms was obtained in comparison with the structure wherein only one gas passage hole of a diameter of 2.5 mm is provided.

Figure 5:
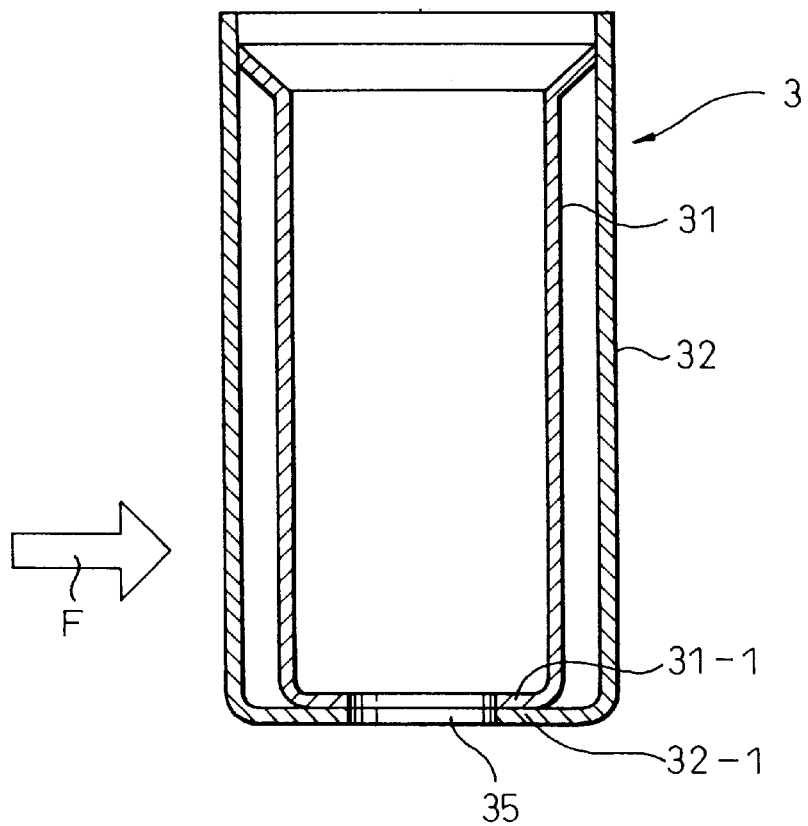
FIG. 5 is a cross sectional view of a cover assembly in a second embodiment of the present invention.
Figure 6:
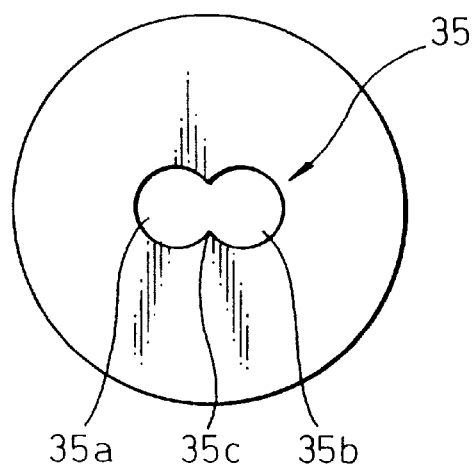
FIG. 6 is a bottom elevational view of a cover in FIG. 5.
Figure 7:
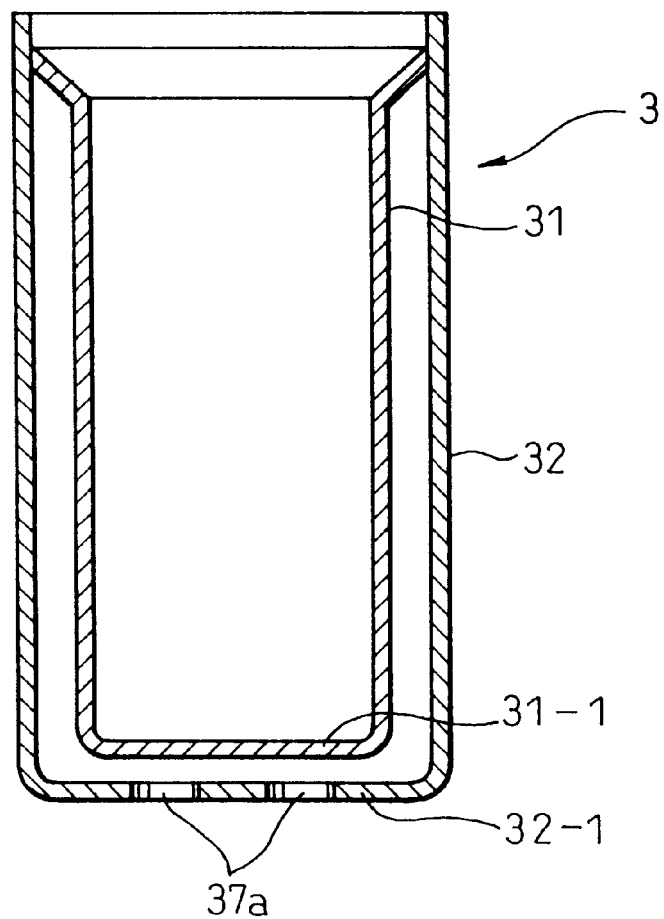
FIG. 7 is a cross sectional view of a cover assembly in a third embodiment of the present invention, taken along line VII—VII in FIG. 8.

FIGS. 5 and 6 show a double wall structure of the cover unit 3 according to the second embodiment. Namely, in the embodiment, a single gas passage hole 35 is provided at the axial bottom end of the cover 3. However, as shown in FIG. 7, the hole 35 is constructed by parts 35a and 35b of a cross-sectional shape of a partial hole, which are juxtaposed along the direction of the flow of the exhaust gas as shown by an arrow F. As a result, a throttled portion 35c is formed at a location where the parts 35a and 35b are connected with each other. As a result of the provision of the throttle portion 35c, one of the parts 35a and 35b of the hole functions as a passageway for introducing a gas, while the other part functions as a passageway for discharging a gas. Thus, the operation obtained is similar to the one explained with reference to the first embodiment.

The inventors have conducted a test of the cover in FIGS. 5 and 6 of the hole portions 35a and 35b of a diameter of 2.5 mm. According to the result of the test as to the response speed, in comparison with the prior art structure having a single hole of a diameter of 2.5 mm of cross sectional shape of a complete circle, an increase in the 63% response speed from 400 ms to 270 mm was obtained.

As will be understood from the above, the gas communication hole must necessarily be plural. Namely, in case where only one hole 35 is provided, the hole 35 is formed with a throttle portion 35c, so that the single hole is separated by the throttle portion into two portions 35a and 35b, in such a manner that one of the portions functions as an inlet opening while the other portion functions as an outlet opening. In this case, the cross sectional shape of the single hole need not necessarily be a connection of two partial holes. Namely, the cross sectional shape may be of three or more partial holes. Furthermore, the hole need not necessarily be circular. Namely, the cross sectional shape of the gas communication hole can be a combination of shapes other than a circular shape such as elliptic shape or polygonal shape. Furthermore, a plurality of the holes of a cross sectional shape as a connection of partial hole can be employed. In this latter case, one of the holes functions as a gas inlet hole, while the other hole functions as a gas discharge hole.

Figure 8:
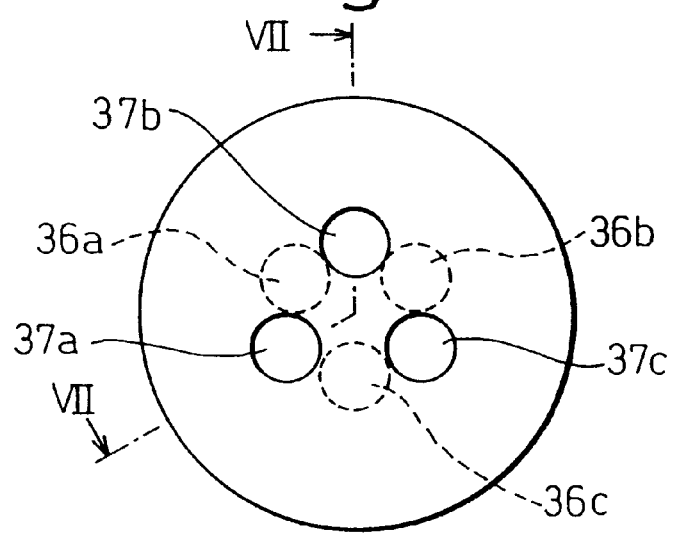
FIG. 8 is a bottom elevational view of a cover in FIG. 7.

FIGS. 7 and 8 show a third embodiment of the present invention, where a space exists between the flat end parts 31-1 and 32-1 of the inner and outer tube 31 and 32 of the cover assembly 3. The flat end 31-1 of the inner tube 31 is formed with gas passage holes 36a, 36b and 36c, while the flat end 32-1 of the outer tube 31 is formed with gas passage holes 37a, 37b and 37c. The gas passage holes 36a, 36b and 36c and 37a, 37b and 37c are arranged alternately between the end parts 31-1 and 32-1. In more detail, as shown in FIG. 8, the holes 36a, 36b and 36c are located at apexes of a first regular triangle, while the holes 37a, 37b and 37c are located at apexes of a second regular triangle which is rotated 60 degree with respect to the first triangle and has a center which is identical to that of the first triangle. The axis of each of the holes 36a, 36b and 36c in the end part 31-1 as well as each of the holes 37a, 37b and 37c in the end part 32-1 are at a location of a spacing of 2 mm from the center of the end parts 31-1 and 32-1. Furthermore, the spacing between the parts 31-1 and 32-1 is 2 mm, which allows the exhaust gas to be introduced into a space inside the inner tube 32.

Due to the above-mentioned staggered arrangement of the holes 36a, 36b and 36c and the holes 37a, 37b and 37c in the inner and outer tubes 31 and 32, an increased heat retaining performance is obtained. In more detail, in comparison with the non-staggered arrangement having three gas passage holes of a diameter of 2 mm, the staggered arrangement in FIG. 8 can obtain a temperature increase of 30° C. at the outer surface of the detecting body 2 and of 15° C. at the inner surface of the cover assembly 3 adjacent the detection body 2. Furthermore, in the structure of the third embodiment in FIGS. 7 and 8, the inner and outer tubes 31 and 32 are, at the end parts 31-1 and 32-1, not contacted with each other, thereby preventing a discharge of the heat from the end 31-1 of the inner tube 31 to the outer tube 32, which otherwise occurs due to a reduced temperature of the outer tube 32 subjected to a contact with the exhaust gas. Thus, an increased heat retaining performance is obtained.

Furthermore, the staggered arrangement can keep substantially unchanged the gas ventilation speed in the cover assembly 3 due to the fact that the each of the inner and outer tubes 31 and 32 is formed with three gas ventilation holes 36a, 36b and 36c or 37a, 37b and 37c, respectively. Thus, a value of 63% response speed as high as 220 ms with respect to a rapid change in the oxygen density is maintained, which is compared with the 63% response speed of 180 ms under the non-staggered arrangement.

Figure 9:
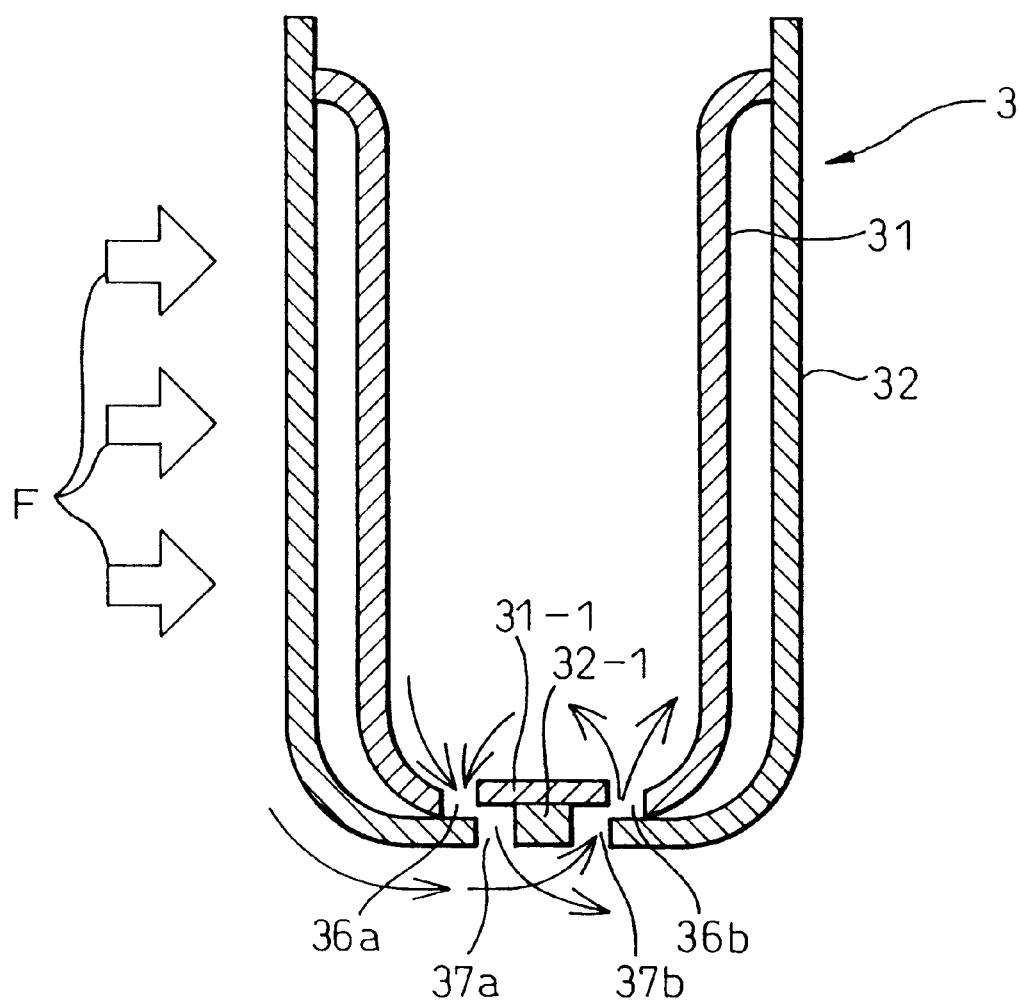
FIG. 9 is a cross sectional view of a cover in FIG. 7.

In a fourth arrangement as shown in FIG. 9, a gap is not provided between the end walls 31-1 and 32-2 of the inner and outer tubes, while the gas vent holes 36a and 36b in the end wall 31-1 of the inner tube 31 and the gas vent holes 37a and 37b in the end wall 32-1 of the outer tube 32 are slightly superimposed, so that the gas in the space inside the cover assembly 3 is ventilated, while keeping a desired heat retaining property.

Figure 10:
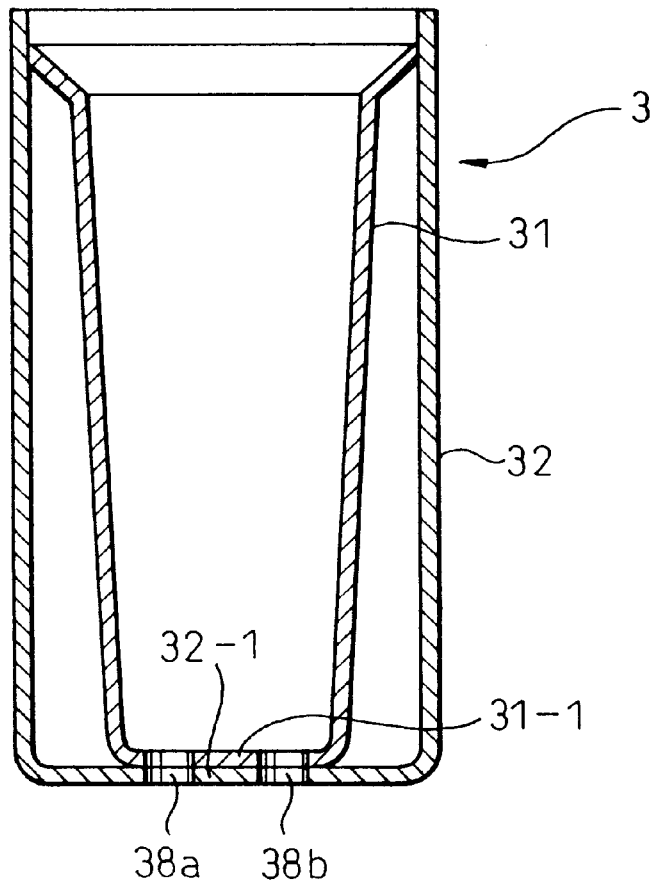
FIG. 10 is a cross sectional view of a cover assembly in a fifth embodiment of the present invention, taken along line X—X in FIG. 11.
Figure 11:
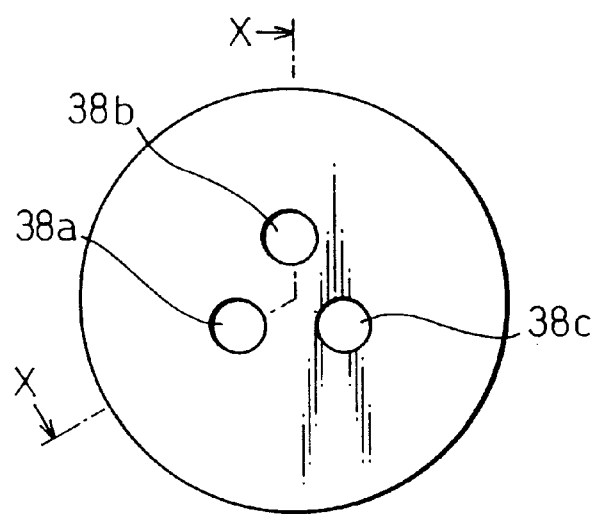
FIG. 11 is a bottom elevational view of a cover in FIG. 10.

FIG. 10 shows a fifth embodiment of the present invention featuring an inner tube 31 which is tapered toward the end wall 31-1 while the outer tube 32 is formed as a straight tube having end wall 32-1, which is in contact with the end wall 31-1 of the inner tube 31. Furthermore, the end walls 31-1 and 32-1 are formed with aligned ventilation holes 38a, 38b and 38c, which are located at apexes of a regular triangle, as shown in FIG. 11. Each of the ventilation holes 38a, 38b and 38c has an inner diameter of about 2 mm and the spacing of the center of the each of the holes is 2 mm.

In the above structure, clue to the downwardly tapered shape of the inner tube 31, a reduction in the volume thereof is obtained, thereby increasing the speed of the gas ventilation. Thus, the 63% response speed upon a rapid change in the oxygen density is increased to 150 ms when compared with that of 180 ms in the straight structure of the inner tube 31.

Figure 12:
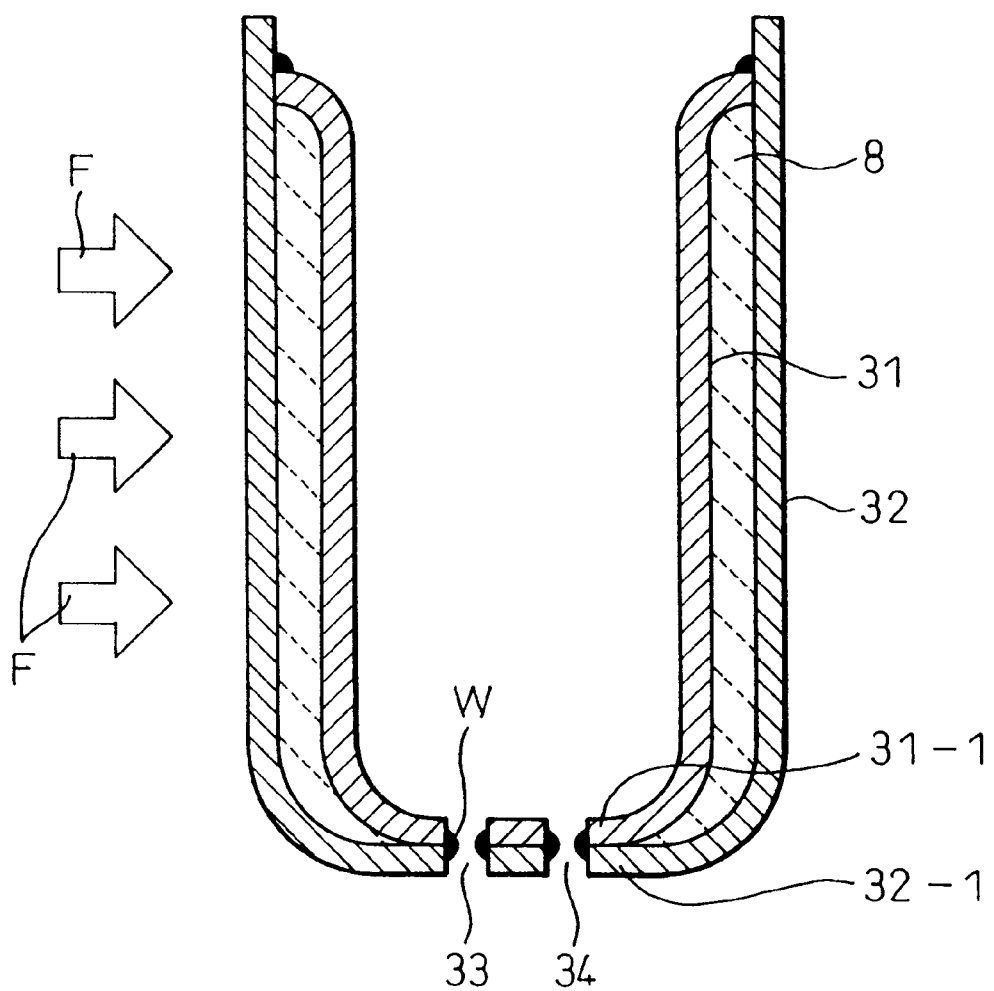
FIG. 12 is a cross sectional view of a cover assembly in a sixth embodiment of the present invention.

FIG. 12 shows a sixth embodiment of the present invention, where the bottom end walls 31-1 and 32-1 of the same structure as that in the first embodiment which are in contact with each other are welded at points W, while a filler such as a pulverized ceramic is filled in the space between the inner and outer tubes 31 and 32 of the cover unit 3.

According to this structure, due to the provision of the filler 8, an improvement in the heat retaining performance is obtained. Furthermore, due to the welded connection between the bottom end walls 31-1 and 32-2 of the inner and outer tubes 31 and 32, the exhaust gas is prevented from remaining in a space otherwise formed between the end walls, thereby increasing a response speed.

Figure 13:
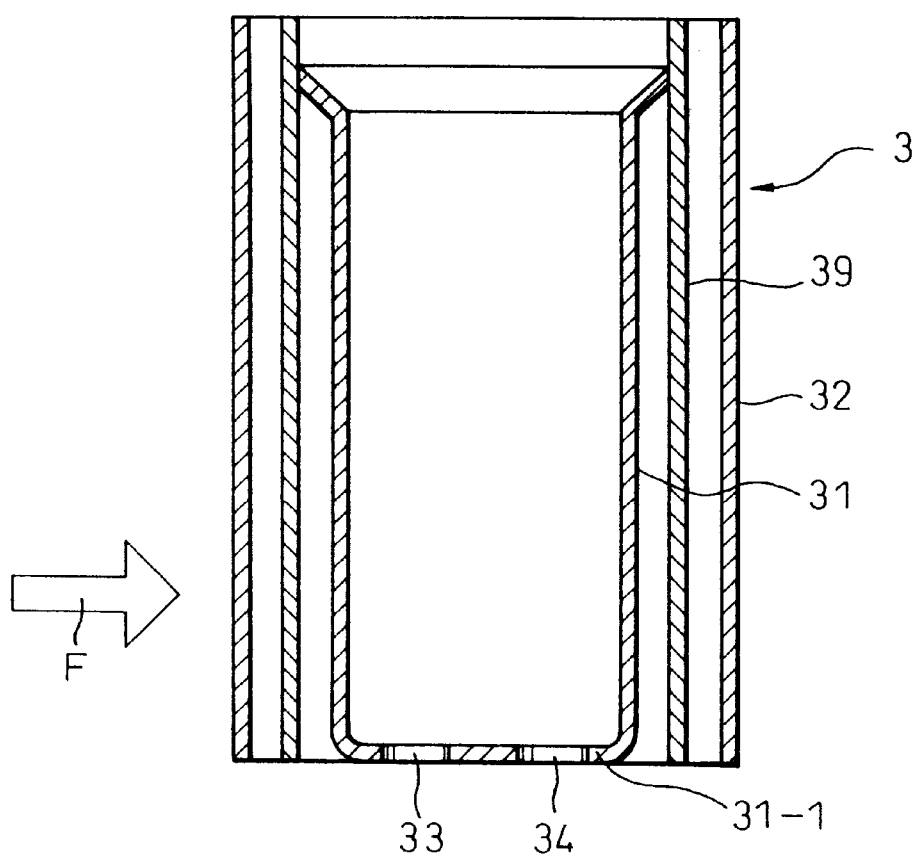
FIG. 13 is a cross sectional view of a cover in a seventh embodiment.
Figure 14:
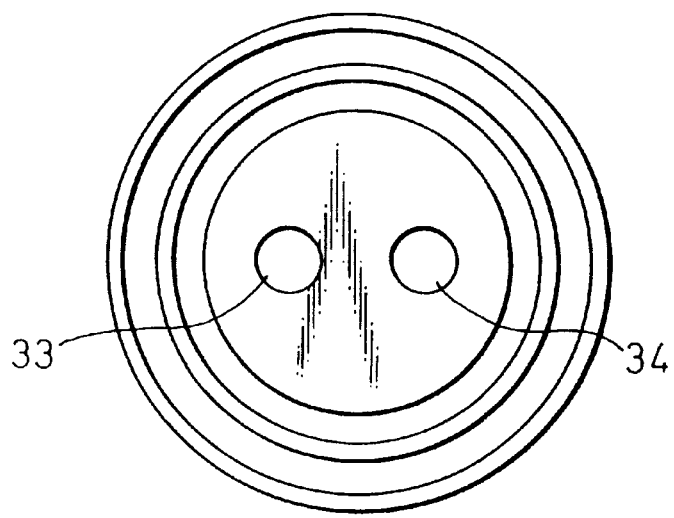
FIG. 14 is a bottom elevational view of the cover in FIG. 13.

FIGS. 13 and 14 show a seventh embodiment of the present invention, where the cover assembly 3 is constructed as a triple wall structure including, in addition to the inner and the outer tubes 31 and 32, a intermediate tube 39. The outer and intermediate tubes 32 and 39 are of the structure which are fully opened at the bottom. In other words, only the inner tube 31 has a bottom wall 31-1 having the vent holes 33 and 34.

According to this embodiment, due to the triple wall structure of the cover assembly 3, an improved heat retaining performance is obtained. Namely, according to the test by the inventor, an increase of temperature of nearly 80° C. is obtained at the location adjacent the gas vent holes 33 and 34 over the double wall structure constructed by the inner and outer tube having the vent holes at the bottom end walls. Furthermore, according to the embodiment, the outer and the intermediate tubes 32 and 39 are, at the bottom ends, fully opened, which prevents the heat at the gas vent holes 33 and 34 from being discharged, via the outer and the intermediate tubes 32 and 39, to the exhaust gas. As a result, a high temperature is maintained at the location adjacent the gas vent holes 33 and 34, which is particularly effective for preventing the holes 33 and 34 from being clogged.

Figure 15:
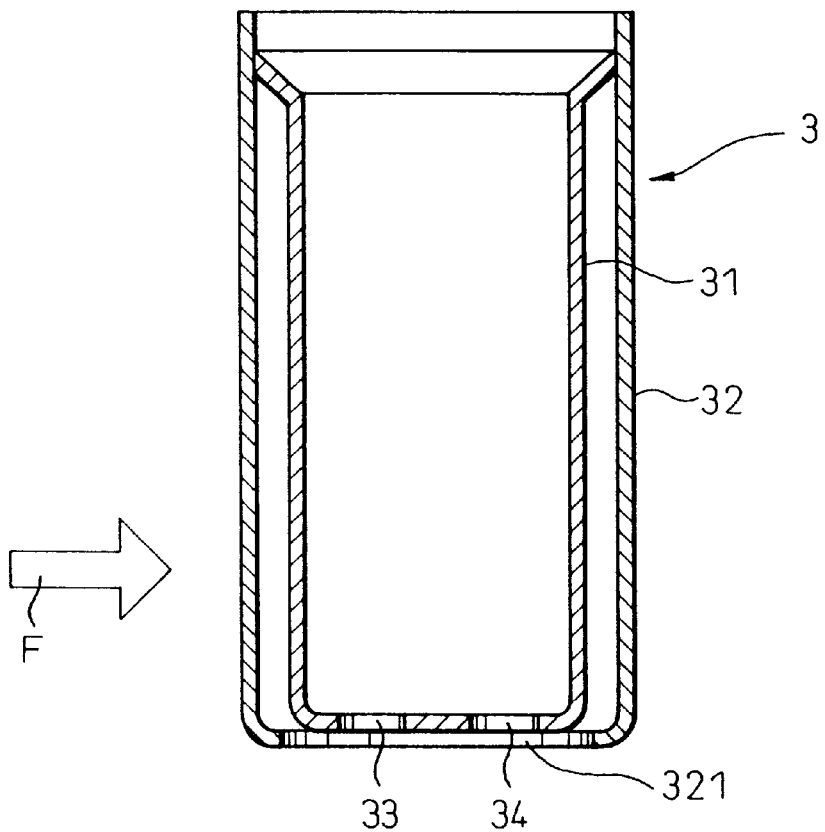
FIG. 15 is a cross sectional view of a cover in an eighth embodiment.
Figure 16:
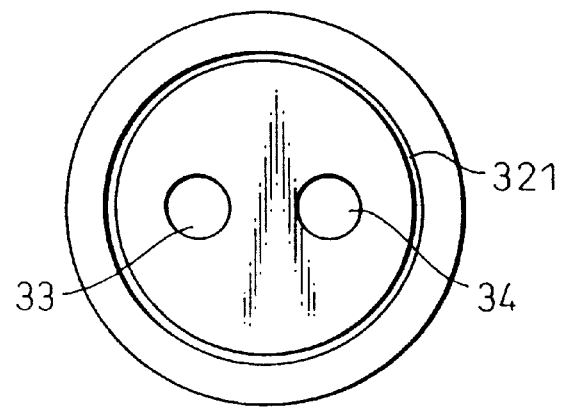
FIG. 16 is a bottom elevational view of the cover in FIG. 15.

FIGS. 15 and 16 show an eighth embodiment of the present invention of the cover assembly 3 formed as a double wall structure having an inner and outer tubes 31 and 32, where the inner tube 31 forms at the bottom end wall gas vent holes 33 and 34, while the outer tube 32 forms at the bottom end wall an opening 321. The opening 321 has a diameter which is large enough for preventing the end of the inner tube 31 from being contacted with the end of the outer tube 32. Even in the structure where the inner tube 31 has the bottom wall, the structure of the inner tube 31 does not contact the outer tube 32 and can prevent the heat in the gas vent holes 33 and 34 from being discharged to the outer tube 32 of a reduced temperature and from being transmitted to the exhaust gas via the side wall of the outer tube 32. Thus, a high temperature is maintained at the location adjacent the gas vent holes 33 and 34, which is effective for preventing the holes from being clogged.

What is claimed is:

1. A device for detecting a concentration of a component in a gas to be detected, comprising:

a gas concentration detecting body which is adapted to be contacted with the gas for generating an electric signal indicative of the concentration of the component; and a cover for covering a portion of the detecting body for preventing the detecting body from being directly subjected to the gas to be detected, said cover having, at an axial end of said cover, a plurality of holes for forming inlet and outlet passageways for the gas to be detected, while said cover forms, at locations other than said axial end, a closed wall not having any holes for a passage of the gas to be detected, and wherein the plurality of holes only at the end of the cover increases a 63% response speed of the device to less than 400 ms.

2. A device according to claim 1, wherein said cover is formed as a double wall structure having an inner and outer tube of different diameters arranged concentrically with each other.

3. A device according to claim 1, wherein said cover is formed as a multiple wall structure having an inner and outer tubes of different diameters and at least one intermediate tube arranged between the inner and the outer tubes, the inner and outer and intermediate tubes being arranged concentrically.

4. A device according to claim 2, wherein only an axial end of the inner tube forms an end wall, where said holes are formed, and any tube located outwardly from the inner tube are fully opened at the axial end.

5. A device according to claim 2, wherein the inner tube, at the axial end, does not contact an axial end of an outer tube.

6. A device according to claim 2, wherein said inner tube is tapered toward said axial end.

7. A device for detecting a concentration of a component in a gas to be detected, comprising:

a gas concentration detecting body which is adapted to be contacted with the gas for generating an electric signal indicative of the concentration of the component; and a cover for covering a portion of the detecting body for preventing the detecting body from being directly subjected to the gas being detected, said cover having, at an axial end of said cover, means for forming inlet and outlet passageways for the gas to be detected, while said cover forms, at locations other than said axial end, a closed wall not having any holes for a passage of the gas to be detected, said means comprising a hole having a throttle portion dividing the hole into the inlet and outlet passageways, and wherein the hole increases a 63% response speed of the device to less than 400 ms.

8. A device according to claim 7, wherein said cover is formed as a double wall structure having an inner and outer tube of different diameters arranged concentrically with each other.

9. A device according to claim 7, wherein said cover is formed as a multiple wall structure having an inner and outer tubes of different diameters and at least one intermediate tube arranged between the inner and the outer tubes, the inner and outer and intermediate tubes being arranged concentrically.

10. A device according to claim 8, wherein only an axial end of the inner tube forms an end wall, where said hole is formed, and any tube located outwardly from the inner tube are fully opened at the axial end.

11. A device according to claim 8, wherein the inner tube, at the axial end, does not contact an axial end of an outer tube.

12. A device according to claim 8, wherein said inner tube is tapered toward said axial end.

* * * * *

UNITED STATES PATENT AND TRADEMARK OFFICE
CERTIFICATE OF CORRECTION

PATENT NO. : 6,202,469 B1  Page 1 of 1
DATED : March 20, 2001
INVENTOR(S) : Satoshi Nakamura, Masanori Yamada, Michihiro Wakimoto, Daisuke Makino, Hideomi Kawachi and Toshihiro Sakawa It is certified that error appears in the above-identified patent and that said Letters Patent is hereby corrected as shown below:

<u>Title page,</u>
Item [73] should read as follows:

-- [73] Assignee: Denso Corporation, Kariya (JP)
                    Nippon Soken, Inc., Nishio (JP) --

Signed and Sealed this

Second Day of April, 2002

*Attest:*

JAMES E. ROGAN
*Attesting Officer*     *Director of the United States Patent and Trademark Office*